(12) United States Patent
Whalen et al.

(10) Patent No.: US 6,551,304 B1
(45) Date of Patent: Apr. 22, 2003

(54) MAGNETIC RETRIEVAL DEVICE AND METHOD OF USE

(75) Inventors: Mark J. Whalen, Alexandria, MN (US); Lloyd K. Willard, Miltona, MN (US)

(73) Assignee: AbbeyMoor Medical, Inc., Miltona, MN (US)

( * ) Notice: Subject to any disclaimer, the term of this patent is extended or adjusted under 35 U.S.C. 154(b) by 206 days.

(21) Appl. No.: 09/724,239

(22) Filed: Nov. 28, 2000

Related U.S. Application Data
(60) Provisional application No. 60/168,306, filed on Dec. 1, 1999.

(51) Int. Cl.⁷ .............................................. A61B 17/00
(52) U.S. Cl. .................. 606/1; 604/523; 604/891.1; 600/29; 600/30; 607/138; 128/840
(58) Field of Search .................. 606/1; 604/93.01, 604/502, 523, 175, 515, 517, 891.1; 607/138, 143; 600/29, 30, 31, 377, 423; 128/840, 839, 841

(56) References Cited

U.S. PATENT DOCUMENTS

| | | |
|---|---|---|
| 651,395 A | 6/1900 | Stapp |
| 1,597,500 A | 8/1926 | Alexander et al. |
| 1,677,671 A | 7/1928 | Councill |
| 1,726,349 A | 8/1929 | Hartsough |
| 1,787,112 A | 12/1930 | King |
| 2,295,848 A | 9/1942 | Jones .......................... 128/303 |
| 2,390,339 A | 12/1945 | Ullman et al. .............. 294/65.5 |
| 2,683,618 A | 7/1954 | Long ........................... 294/65.5 |
| 2,687,131 A | 8/1954 | Raiche ........................ 128/349 |
| 2,853,075 A | 9/1958 | Hoffman et al. ............. 128/356 |
| 2,943,626 A | 7/1960 | Dormia ....................... 128/328 |
| 3,042,030 A | 7/1962 | Read ........................... 128/127 |
| 3,332,425 A | 7/1967 | Luborsky et al. ........... 128/356 |
| 3,472,230 A | 10/1969 | Fogarty ...................... 128/328 |
| 3,791,387 A | 2/1974 | Itoh ............................ 128/320 |
| 3,805,777 A | 4/1974 | Ansari ........................ 128/130 |
| 3,812,841 A | 5/1974 | Isaacson ........................ 128/1 |
| 3,828,790 A | 8/1974 | Curtiss et al. .............. 128/320 |
| 3,908,646 A | 9/1975 | Ansari ........................ 128/130 |
| 4,572,162 A | 2/1986 | Livesay et al. ................ 128/1 |
| 4,610,657 A | 9/1986 | Densow ........................ 604/8 |
| 4,671,795 A | 6/1987 | Mulchin ..................... 604/281 |
| 4,781,677 A | 11/1988 | Wilcox ........................ 604/28 |
| 4,790,809 A | 12/1988 | Kuntz ........................... 604/8 |
| 4,865,030 A | 9/1989 | Polyak ........................ 128/321 |
| 4,946,449 A | 8/1990 | Davis, Jr. ................... 604/256 |
| 4,955,859 A | 9/1990 | Zilber ........................... 604/8 |
| 4,973,301 A | 11/1990 | Nissenkorn ..................... 604/8 |
| 5,003,608 A | 3/1991 | Carlson ...................... 381/68.6 |
| 5,112,306 A | 5/1992 | Burton et al. ............... 604/101 |
| 5,250,029 A | 10/1993 | Lin et al. ...................... 604/96 |

(List continued on next page.)

OTHER PUBLICATIONS

R. S. Munro and F. B. Scott, *Use of Completely Implantable Urethral Catheter in Male Patients with Spinal Cord Injury*, Urology, Nov. 1976 at 492.

*Primary Examiner*—Teresa Walberg
*Assistant Examiner*—Fadi H. Dahbour
(74) *Attorney, Agent, or Firm*—Nawrocki, Rooney & Sivertson, P.A.

(57) ABSTRACT

Apparatus and method for retrieving a remotely located device equipped with a magnetic coupler is provided. The apparatus includes a magnetic coupling carried at an end of an elongate member for attracting the magnetic coupler of the remotely located device, and aligning the magnetic coupler with the magnetic coupling. A frictional engagement device, substantially housing the magnetic coupling therein, is adapted for trapping the magnetic coupler therein such that a retrieval force applied to the apparatus is transferred to the remotely located device via the frictional engagement device to thereby facilitate sure retrieval of the device as by magnetic mechanical entrapment.

27 Claims, 5 Drawing Sheets

U.S. PATENT DOCUMENTS

| | | | | |
|---|---|---|---|---|
| 5,360,402 A | | 11/1994 | Conway et al. | 604/97 |
| 5,562,598 A | * | 10/1996 | Whalen et al. | 600/29 |
| 5,624,374 A | * | 4/1997 | Von Iderstein | 600/29 |
| 5,697,866 A | * | 12/1997 | Von Iderstein | 600/59 |
| 5,711,314 A | * | 1/1998 | Ardito | 600/29 |
| 5,713,877 A | * | 2/1998 | Davis | 600/29 |
| 6,027,442 A | * | 2/2000 | Von Iderstein | 600/29 |
| 6,066,088 A | * | 5/2000 | Davis | 600/29 |
| 6,171,298 B1 | * | 1/2001 | Matsuura et al. | 604/891.1 |
| 6,183,461 B1 | * | 2/2001 | Matsuura et al. | 604/502 |
| 6,293,923 B1 | * | 9/2001 | Yachia et al. | 604/93.01 |

* cited by examiner

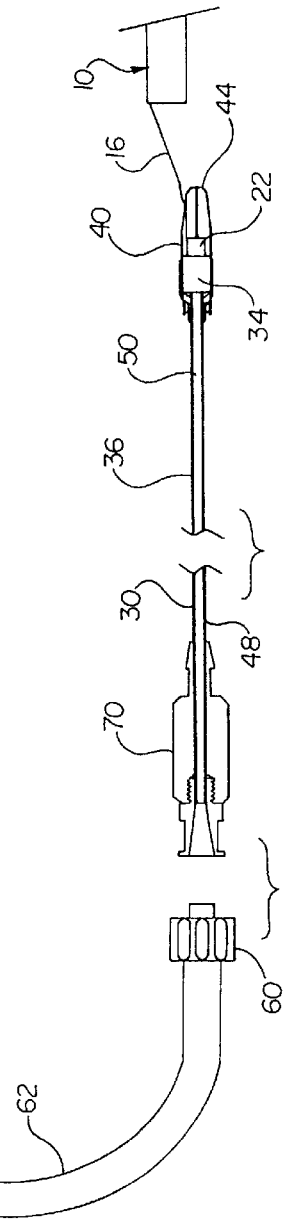
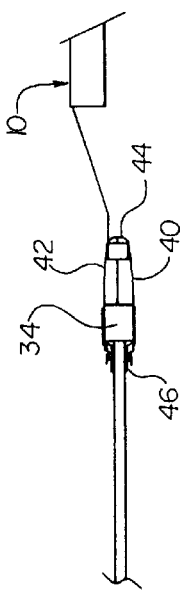
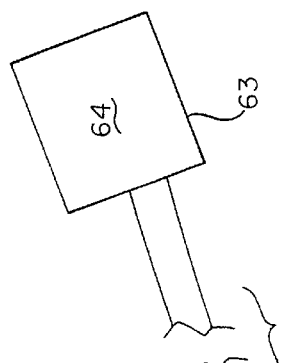
Fig.2
Fig.2A

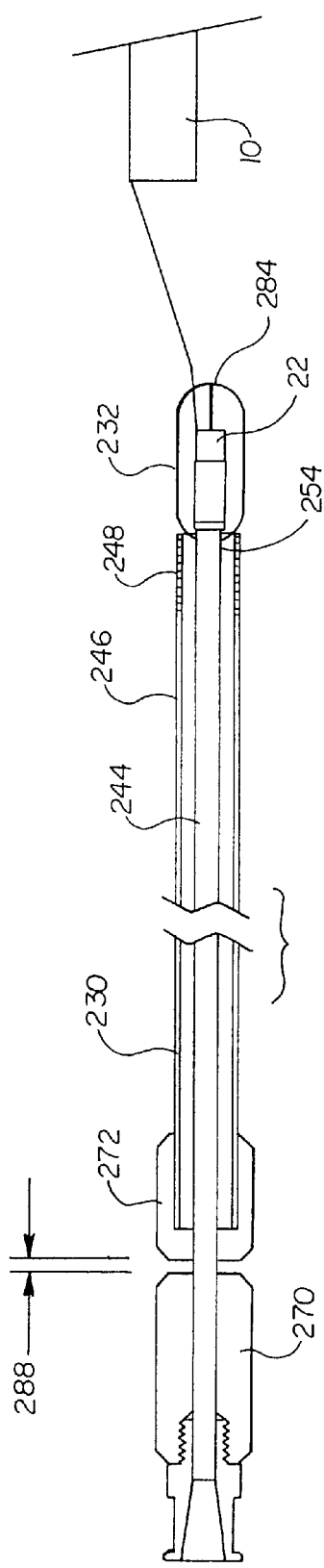
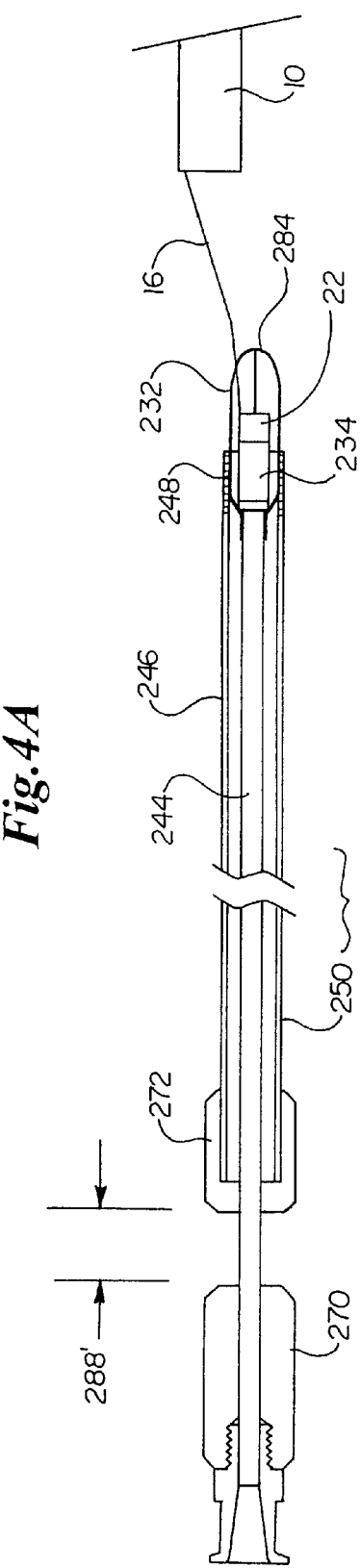

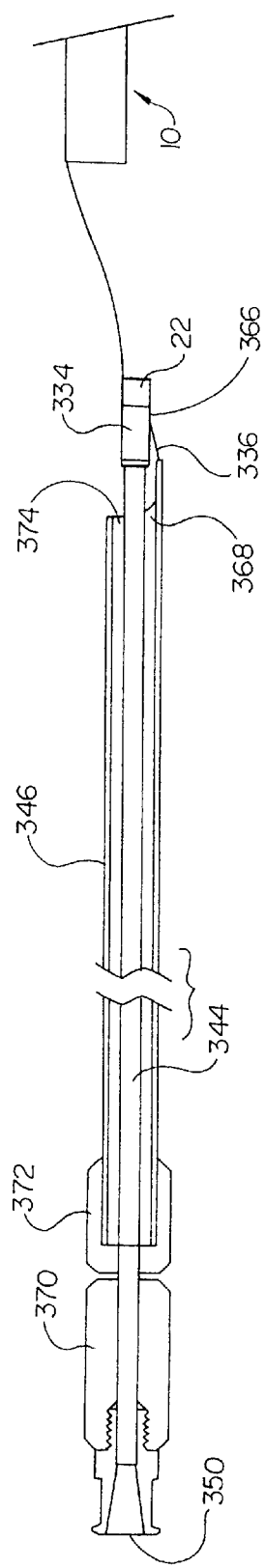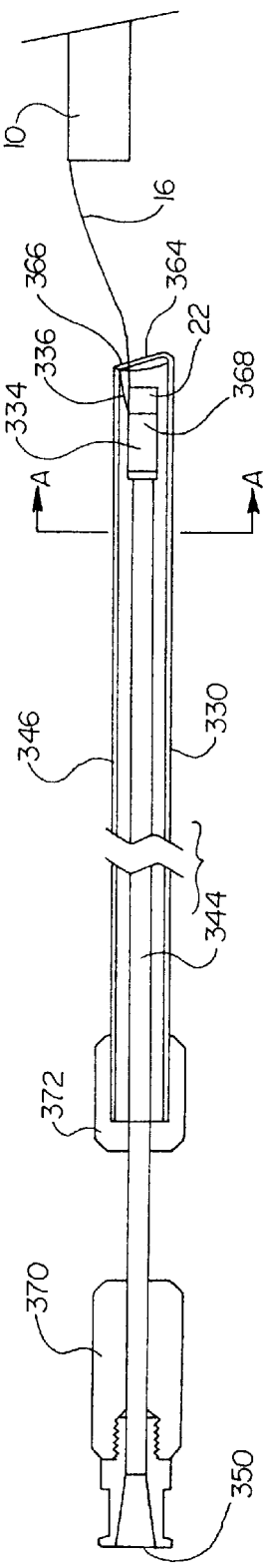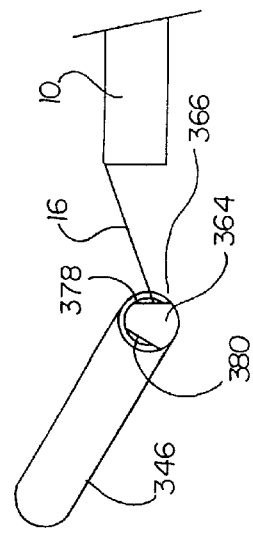
*Fig.5*
*Fig.5A*
*Fig.5B*

MAGNETIC RETRIEVAL DEVICE AND METHOD OF USE

This is a regular application filed under 35 U.S.C. §111(a) claiming priority under 35 U.S.C. §119(e)(1), of provisional application Ser. No. 60/168,306, filed Dec. 1, 1999 under 35 U.S.C. §111(b).

BACKGROUND OF THE INVENTION

The following disclosure relates to an apparatus and method for retrieving a device which is positioned within a remote location. This location is preferably located within the human body, and more preferably within the human urethra.

The subject invention provides for apparatus and methods for retrieving devices remotely when access otherwise would require more expensive and/or complex procedures such as optical viewing, ultrasonic detection, x-ray, fluoroscopy and grasping with a forceps. Remote (i.e. indwelling) devices may be of many configurations, with medical or other industrial applications. With human medical applications, the remote device could consist of, though not be limited to, intraurethral devices such as stents, shunts or valved devices. Urethral (or uteral) devices may be sized from a total profile in diameter from 2 to as large as 40 French, with device length likely to vary according to the application.

Features and methods of the embodiments of this application may be compatible with the following co-pending applications, incorporated herein by reference: URETHRAL DEVICE WITH ANCHORING SYSTEM, Ser. No. 09/411,491, filed Oct. 4, 1999; URETHRAL APPARATUS WITH POSITION INDICATOR AND METHODS OF USE THEREOF, Ser. No. 90/340,491, filed Jun. 30, 1999; MAGNETICALLY LATCHED DEFORMABLE DOME URINARY FLOW CONTROL APPARATUS AND METHOD OF USE THEREOF, Ser. No. 60/179,038 filed Feb. 1, 2000.

SUMMARY OF THE INVENTION

Apparatus and method for retrieving a remotely located device equipped with a magnetic coupler is provided. The apparatus includes a magnetic coupling carried at an end of an elongate member for attracting the magnetic coupler of the remotely located device, and aligning the magnetic coupler with the magnetic coupling. A frictional engagement device, substantially housing the magnetic coupling therein, is adapted for trapping the magnetic coupler therein such that a retrieval force applied to the apparatus is transferred to the remotely located device via the basket to thereby facilitate sure retrieval of the device as by magnetic mechanical entrapment.

More specific features and advantages obtained in view of those features will become apparent with reference to the drawing figures and DETAILED DESCRIPTION OF THE INVENTION.

BRIEF DESCRIPTION OF THE DRAWINGS

FIG. 2 schematically shows a portion of the remotely deployed device coupled to the apparatus of FIG. 1;

FIG. 2A schematically shows the magnetic coupler captured within the basket of the apparatus of FIG. 1, and axially aligned with respect to the magnetic coupling;

FIGS. 4 and 4A schematically show a further embodiment of the subject invention illustrating the relationship between the basket and the magnetic coupling, namely that the basket is capable of radial collapse upon being selectively axially retracted relative to the magnetic coupling; and, FIGS. 5, 5A and 5B schematically show yet another embodiment of the subject invention illustrating a non-basket mechanical capture structure.

DETAILED DESCRIPTION OF THE INVENTION

Figure 1:
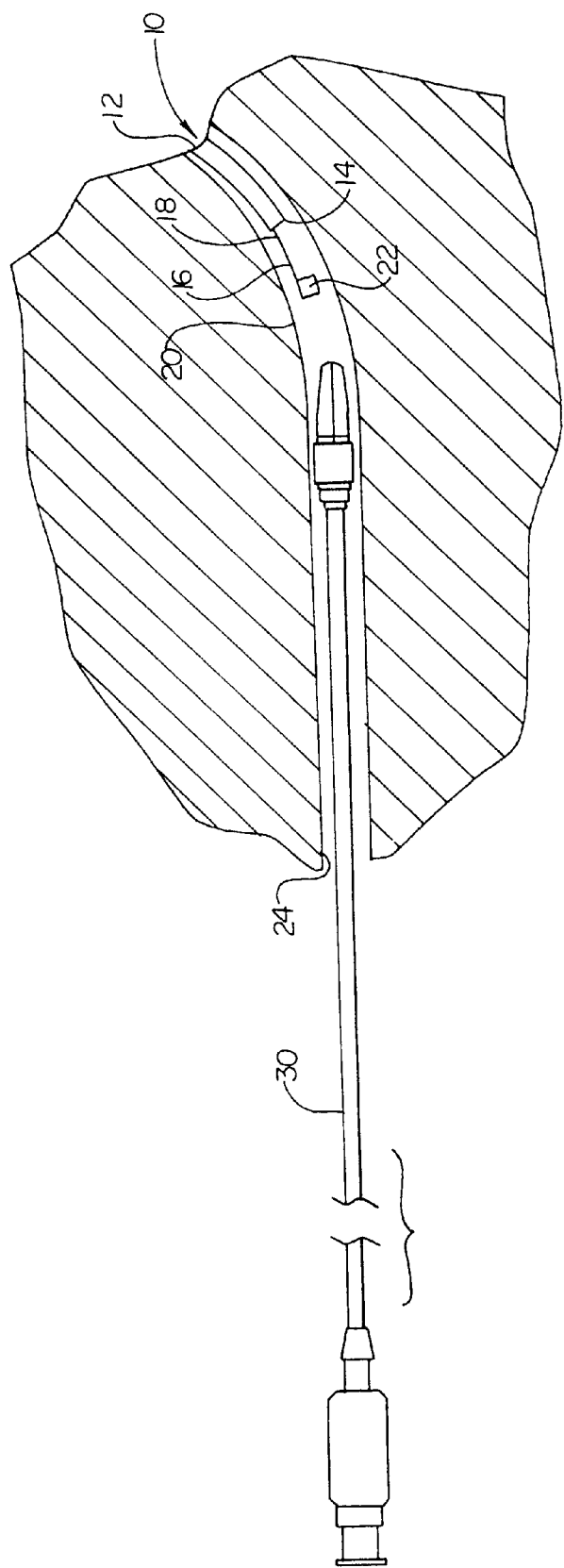
FIG. 1 schematically shows the apparatus of the subject invention being advanced toward a remotely deployed device for which retrieval is sought.

The apparatus and method of this invention requires only simple equipment. The securing is accomplished by a simple magnetic coupling apparatus incorporated functionally with the remote device. FIG. 1 illustrates the remote device. The remote device 10 is equipped with a tether 16 at distal extremity 14 from the remote device 10 within passageway 24 as illustrated in FIG. 1. A magnetic coupler 22 is attached distally to tether 16. This magnetic coupler 22 is constructed of a material that is magnetic in properties, or further is magnetized.

The tether 16 is sized and secured in a manner such that it has sufficient mechanical strength to withstand the force required to pull the remote device from the location and its specific environment through the necessary passageway 24. The size of the device and the environment of the passageway 24 will determine the mechanical requirements of the tether 16 and the method of attachment. The magnetic coupler 22 is linked magnetically with the retrieval tools as illustrated by the disclosed embodiments of retrieval devices. FIG. 1 illustrates the retrieval tool 30 of the first embodiment located within passageway 24 near the distal extremity 14 of remote device 10.

FIG. 1 illustrates an example of a indwelling device 10 which is retrievable from a urinary tract environment. The indwelling device 10 consists of a proximal extremity 12, and a distal extremity 14. The tether 16 has a proximal extremity 18, and a distal extremity 20. Tether proximal extremity 18 is secure at distal extremity 14 of indwelling device 10. A magnetic coupler 22 is secured to distal extremity 20 of tether 16. This magnetic coupler 22 is constructed of a material that is magnetic in properties, or magnetized. Tether 16 may be secured to the magnetic coupler 22 at any radial orientation. Securing of the tether 16 radially away from the magnetic coupler 22 centerline provides a torque upon separation which is useful in entrapment. The preferred magnetic material for magnetic coupler 22 is magnetized Samarium Cobalt 20, whereas the preferred magnetic material for magnetic coupling 34 magnetization is Neodynium 27. All the magnetic materials are preferably coated with a suitable coating for biocompatable inertness such as Class VI epoxy or vapor deposited paraxylene.

Tether 16 is sized and secured in a manner such that it has sufficient mechanical strength to withstand the force required to pull the indwelling device from the location and its specific environment through the necessary passageway 24. The size of the device and the environment of the passageway 24 will determine the mechanical requirements of the tether 16 and the method of attachment. The preferred material for the retrieval tether is USP class VI silicone coated braided silk suture in a size 1/0. This suture size provides a break load maximum of 8.6 pounds which is more than sufficient for most applications.

FIG. 2 illustrates an expanded partial sectional view of retrieval device 30 of the first embodiment in a coupled state with indwelling device 10. Amplification device 64 is further shown uncoupled. The amplification device 64 assists the blind coupling procedure by providing an audible feedback when coupling occurs between magnetic coupling 34 and magnetic coupler 22 of indwelling device 10. During the retrieval procedure, a retrieval device 30 is advanced towards the magnetic coupler 22 of the indwelling device 10. As the retrieval device 30 is provided with a magnetic coupling 34, when the retrieval device 30 of the preferred embodiment is advanced to the proximity of the magnetic coupler 22, the magnetic coupler 22 is drawn towards the magnetic coupling 34 of the retrieval device 30. The retrieval device of this embodiment is configured for retrieval by the use of a basket 40 which allows for retrieval without manipulation of any moving parts within the retrieval device 30.

Referring to FIGS. 1, 2 and 2a, the construction of the retrieval device 30 is herein described from the proximal extremity 44 toward the distal extremity 48. Basket 40 extends from magnet housing 46 which is attached to elongate member 36 to proximal extremity 44. Magnet coupling 34 is shown located within basket 40. Hub 70 is secured near distal extremity 48 of elongate member 36.

The retrieval of the indwelling device 10 is accomplished when the retrieval device 30 is advanced within the passageway 24 (FIG. 1). Retrieval device 30 is advanced towards indwelling device 10 until magnetic coupling 34 and the magnetic coupler 22 are attracted and move towards each other vis-a-vis cooperation of their magnetic fields. The tether 16 is flexible and thus provides for freedom of movement of the magnetic coupler 22. The magnetic coupler 22 and the magnetic coupling 34 will then mate. The magnetic fields between the magnetic coupler 22 and the magnetic coupling 34 cause the axis of the magnetic coupler 22 and the magnetic coupling 34 to align. Mating of the magnetic coupling 34 of the retrieval device 30 and the indwelling device 10 via coupler 22 may provide sufficient force when each are magnetically linked to allow for the removal of the indwelling device without separating. In many applications it may be desirable to minimize the size of the tether 16 and the magnetic coupler 22 on the indwelling device 10. For this reason the separation force is relatively low, and perhaps inadequate to allow for removal of the indwelling device 10. When minimization of the size of the tether 16 and magnetic coupler 22 is desirable, as it is in the urethral application, there is a need to grasp the magnetic coupler 22 to assure adequate gripping to allow removal to be facilitated. To provide much greater security in the retrieval process, basket 40 provides for the entrapment of magnetic coupler 22. When the retrieval device 30 is withdrawn, if the magnetic coupler 22 and the magnetic coupling 34 separate, the magnetic field will keep magnetic coupler 34 aligned with the magnetic coupling 34 axis, even though it is separated. The tension caused by the tether 16 on the indwelling device, and the magnetic field in the distal direction causes the magnetic coupler 22 to move toward proximal extremity 44 of basket 40. The proximal extremity 44 of basket 40 is preferably parabolic at the proximal extremity. The magnetic coupler 22 is then entrapped in basket 40. Withdrawal of retrieval device 30 causes indwelling device 10 to be pulled from the remote location.

FIG. 2A illustrates a sectional view of basket 40 with magnetic coupler 22 entrapment within basket 40 at proximal extremity 44. Basket members 42 converge at proximal extremity 44 and distally in magnet housing 46. The plurality of basket members 42 may be comprised of either three, or four, or more members depending upon the application. The preferred quantity is four in the male intraurethral application. Each of the basket members 42 are preferably formed of 0.008 inch diameter round wire made of 304V stainless steel. The individual basket members 42 are located evenly spaced around the perimeter according to their number. In the preferred embodiment a quantity of four basket members 42 are spaced orbitally, 90 degrees apart. Each of the basket members is covered by PTFE (teflon) tubing 0.010 inches in inner diameter and 0.022 inches outer diameter.

Another feature of the device of FIG. 2 is that rotation of retrieval device 30 further causes the tether 16 to pull the magnetic coupler 22 into the proximal extremity 44 of basket 40. This gives further securing prior to removal of the retrieval device 30 and indwelling device 10.

Yet another useful. feature selectively incorporatable within all the embodiments is audible coupling feedback. When coupling of retrieval device 30 occurs, magnetic coupling 34 and magnetic coupler 22 produce a instantaneous acoustical vibration. This vibration is audible when indwelling device 10 is in an environment which does not excessively dampen sound. If the indwelling device 10 and retrieval device 30 are in a severe sound or vibration dampening environment, sound amplification may be necessary to detect the coupling event. The device of the first embodiment is provided with a passageway 50 within elongate member 36. Hub 70 is provided in the form of a female luer fitting. When audible feedback confirming connection is desired hub 70 is than connected to female luer fitting 60 which provides the acoustical conduit to tube 62. Amplification device 64 is further interfaced at the distal end 63 of tube 62. Upon coupling, magnetic coupling 34 with magnetic coupler 22, sound is generated. The sound waves are transmitted distally through elongate member 36 toward distal extremity 48. Sound waves continue to travel, entering female luer fitting 60 through tube 62, to amplification device 64. A stethoscope is the preferred amplification device. It is obvious to those skilled in the art that amplification device 64 may be accomplished by functionally equivalent devices to that of a stethoscope. Once sound waves impinge upon device 64, the signal may be filtered, amplified, either in analog or digital format, and manipulated in ways to provide audible, optical, or other sensory outputs. The sound may be transmitted either through a hollow, or solid, or liquid transmission medium. Alternatively, amplification device 64 may be located at any location distal of the distal face of magnetic coupler 22.

When greater amplification is needed than a level that is audibly discernible by a standard stethoscope to detect the coupling, an amplified stethoscope provides for those requirements. Amplified stethoscopes further provide band pass sound filtration capabilities which allow for the removal of frequencies which are outside the sound frequency band of the coupling event. Interface to standard single or dual tube stethoscopes is easily achieved by inserting either a single or "Y" barbed luer into the stethoscope tubing and inserting the opposite barbed fitting into tube 62. This apparatus and method of sound detection of the coupling event is effective in each of the embodiments described in FIGS. 2–5.

Figure 3:
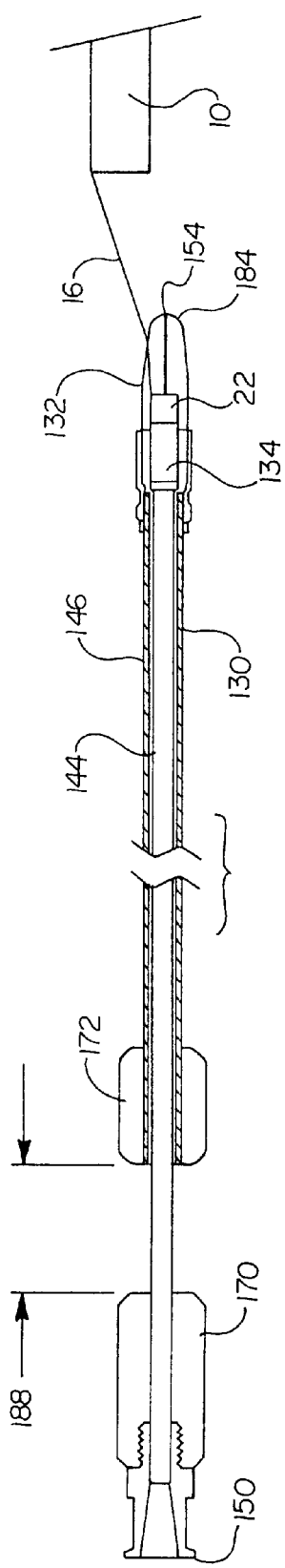
FIGS. 3 and 3A schematically show an alternate embodiment of the subject invention illustrating the relationship between the basket and the magnetic coupling, the basket being selectively axially retractable relative to the magnetic coupling.
Figure 3A:
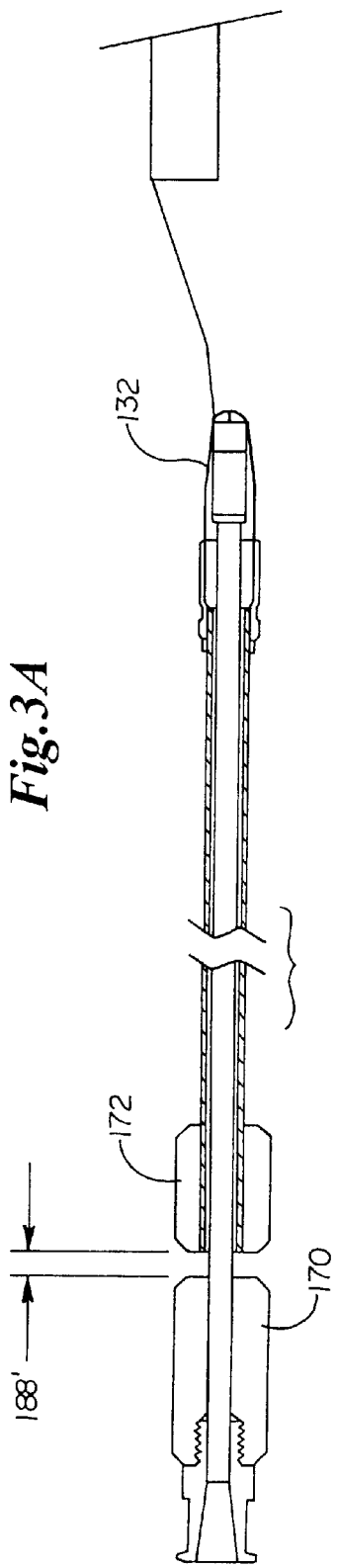

Referring to FIGS. 3 and 3A, the second embodiment of the retrieval device of the subject invention functions in similar manner as the device of FIG. 2. Although the retrieval device 130 is provided with a basket 132 which is used in retrieval, the device of this second embodiment provides for axial and radial movement of basket 132. The sequence of mating magnetic coupling 134 with magnetic coupler 22 is identical to that of the first embodiment. FIG. 3A illustrates that upon the mating being accomplished, basket 132 is moved relatively toward distal extremity 150 along the longitudinal axis of first elongate member 144 by securing first elongate member 144 and retracting second elongate member 146. This results in the securing of magnetic coupler 22 within basket 132. The relative movement is evidenced by the difference in spacing magnitude of gap 188 on FIG. 3, and gap 188' on FIG. 3A.

Though the mating of magnetic coupling 134 of the retrieval device 130 and the magnetic coupler 22 of remote device 10 may provide sufficient force when they are magnetically linked to allow for the removal of the remote device without separating, basket 132 is the primary retrieval structure. Like the first and second embodiments, when the retrieval tool 130 is withdrawn, if the magnetic coupler 22 and the magnetic coupling 134 separate, the magnetic field will keep magnetic coupler 22 aligned with the magnetic coupling 134 axis, even though it is separated. The tension caused by the tether 16 on the remote device 10, and the magnetic field in the distal direction causes the magnetic coupler 22 to move toward proximal extremity 184 of basket 132. The proximal extremity 184 of basket 132 is radiused at the proximal extremity 184. The magnetic coupler 22 is then entrapped in the basket 132. Withdrawal of retrieval device 130 causes remote device 10 to be pulled from the remote location.

Another common feature of the device of FIG. 3 with that of FIG. 2, is that rotation of retrieval tool 130 further causes the tether to pull the magnetic coupler 22 into the proximal extremity 184 of basket 132. This offers further security prior to removal of the retrieval tool 130 and remote device 10.

Referring to FIGS. 4 and 4A, retrieval device 230 of this embodiment functions in similar manner as the devices of the previous embodiments. The retrieval device 230 is provided with a basket 232 which allows and enables the retrieval or remote device 10. The device of this third embodiment provides for axial and radial movement of basket 232. The retrieval device 230 of this embodiment utilizes radial closure of the basket 232.

The distal termination 252 of basket 232 is on first elongate member 244. When second elongate member 246 is displaced towards proximal extremity 284, while first elongate member 244 is held stationary, collet ring 248 forces radially-inward basket 232. FIG. 4A illustrates the basket members 256 in the uncompressed position and FIG. 4A illustrates the basket members 256 in the compressed position. Gap 288 of FIG. 4 and gap 288' FIG. 4A illustrate the relative movement at inner hub 270 and outer hub 272. As illustrated, the basket 232 deforms radially as the distal termination 252 of basket 232 is forced beneath collet ring 248. The magnetic coupler 22 is retained within basket 232. In like manner with the previous two embodiments, though the magnetic coupling 234 of the retrieval device 230 and the remote device mating may provide sufficient force when they are magnetically linked to allow for the removal of the remote device without separating, basket 232 is the primary retrieval mechanism. Like the first and second embodiments, when the retrieval tool 230 is withdrawn, if the magnetic coupler 22 and the magnetic coupling 234 separate, the magnetic field will keep magnetic coupler 234 aligned with the magnetic coupling 234 axis, even though it is separated. The tension caused by the tether 16 on the remote device 10, and the magnetic field in the distal direction causes the magnetic coupler 22 to move toward proximal extremity 244 of basket 232. The proximal extremity 244 of basket 232 is radiused at the proximal extremity. The magnetic coupler 22 is then entrapped in the basket. Withdrawal of retrieval device 230 causes remote device 10 to be pulled from the remote location.

Another common feature of the device of FIG. 4 with that of FIGS. 2 & 3, is that rotation of retrieval tool 230 further causes the tether to pull the magnetic coupler 22 into the proximal extremity 244 of basket 232. This offers further security prior to removal of the retrieval tool 230 and remote device 10.

FIGS. 5, 5A and 5B illustrate a fourth embodiment of the subject invention. The sequence of mating of magnetic coupling 334 with magnetic coupler 22 is identical to that of the previous embodiment. Upon the mating being accomplished, distal inner hub 370 is moved in the distal extremity 350 relative to distal outer hub 372. First elongate member 344 is secured near the distal extremity 350 to distal inner hub 370 and near the proximal extremity to magnetic coupling 334. Strap(s) 336 are comprised of silk 1/0 suture which are flexible and strong and extend from distal termination 368 to proximal termination 366. When distal inner hub 370 is moved in the direction of distal extremity 350 relative to distal outer hub 372, magnetic coupling 334 enables passage of magnet 18 of retrieval device 10 into passageway 374 of second elongate member 346. When this movement occurs the strap(s) 336 are placed in tension by the relative movement of the distal termination 368 while proximal termination point 366 remains fixed.

FIG. 5a illustrates the containment of magnetic coupler 22 within passageway 374 of second elongate member 346 of retrieval device 330. The proximal end 364 of second elongate member 346 is deflected toward the direction of distal extremity 350. Retraction of proximal extremity 364 of second elongate member 346 results in its deflection and closure. FIG. 5b illustrates a partial view along line A—A. A recess 380 projects around at least a portion of the perimeter. Tether 16 is secured to magnetic coupler 22 which is encapsulated within second elongate member 346 and extends out of proximal extremity 364 through recess 380. When retrieval device 330 is withdrawn in a manner consistent with the all embodiments, proximal extremity 364 retains magnetic coupler 22 in place when distal inner hub 370 is manually or mechanically maintained in the direction towards distal extremity 350 relative to distal outer hub 372. This invention disclosure provides device configurations which achieve this function and method. There are other variations of this invention which will become obvious to those skilled in the art. It will be understood. that this disclosure, in many respects, is only illustrative. Changes may be made in details, particularly in matters of shape, size, material, and arrangement of parts without exceeding the scope of the invention. Accordingly, the scope of the invention is as defined in the language of the appended claim.

What is claimed is:

1. Apparatus for retrieving a remotely located device equipped with a magnetic coupler, said apparatus comprising:
    a. a magnetic coupling carried at an end of an elongate member for attracting the magnetic coupler of the remotely located device, and aligning the magnetic coupler with said magnetic coupling for cooperative engagement with said magnetic coupling; and,
    b. a frictional engagement device substantially housing said magnetic coupling therein, said frictional engagement device adapted for trapping the magnetic coupler therein such that a retrieval force applied to said apparatus is transferred to the remotely located device via said frictional engagement device to thereby facilitate sure retrieval of the device as by magnetic mechanical entrapment.

2. The apparatus of claim 1 wherein said frictional engagement device extends at least partially from said end of said elongate member.

3. The apparatus of claim 2 further comprising a sheath surrounding said elongate member, and axially aligned therewith for axial adjustment with respect thereto, said frictional engagement device being radially collapsible within said sheath upon select adjustment of said sheath.

4. The apparatus of claim 2 wherein said frictional engagement device has a free end, said free end being radiused.

5. The apparatus of claim 4 wherein said magnetic coupler is capable of being trapped at said free end of said frictional engagement device during retrieval of the remotely located device.

6. The apparatus of claim 2 wherein said frictional engagement device has a free end, said free end having a parabolic configuration.

7. The apparatus of claim 6 wherein said magnetic coupler is capable of being trapped at said free end of said frictional engagement device during retrieval of the remotely located device.

8. The apparatus of claim 2 wherein said frictional engagement device comprises a plurality of frictional engagement device members.

9. The apparatus of claim 8 wherein said frictional engagement device comprises four frictional engagement device members.

10. The apparatus of claim 8 wherein each of the members of said plurality of frictional engagement device members are of stainless steel construction.

11. The apparatus of claim 1 further comprising a sheath surrounding said elongate member, and axially aligned therewith for axial adjustment with respect thereto, said frictional engagement device extending from an end of said sheath for axial movement therewith.

12. The apparatus of claim 1 wherein said apparatus further includes an amplification device adapted to be linked to said elongate member so as to augment an audio signal resulting from mating of the magnetic coupler with said magnetic coupling, thereby providing aural indicia of device capture in anticipation of retrieval.

13. The apparatus of claim 12 wherein said amplification device is a stethoscope.

14. Apparatus for retrieving remotely deployed medical devices from a mammalian body, the devices having a magnetic coupler, said apparatus comprising:
   a. a magnetic coupling carried at an end of an elongate body for at least initially attracting the magnetic coupler of the remotely located device and aligning the magnetic coupler with said magnetic coupling for cooperative engagement with said magnetic coupling; and,
   b. means for mechanically retaining the initially attracted and aligned magnetic coupler such that a retrieval force applied to said apparatus is transferred to the remotely located device via said means to thereby facilitate sure retrieval of the device as by magnetic mechanical entrapment.

15. The apparatus of claim 14 wherein said means for mechanically retaining the initially attracted and aligned magnetic coupler is a frictional engagement device, said frictional engagement device substantially housing said magnetic coupling therein.

16. The apparatus of claim 15 wherein said apparatus further includes means for manipulating said frictional engagement device in furtherance of secure capture of the magnetic coupler within said frictional engagement device throughout a retrieval procedure.

17. The apparatus of claim 16 wherein said manipulation includes selective axial translation of at least a portion of said means for mechanically retaining the initially attracted and aligned magnetic coupler relative to said magnetic coupling.

18. The apparatus of claim 17 wherein said means for manipulating said frictional engagement device in furtherance of secure capture of the magnetic coupler within said frictional engagement device comprises a second elongate body, said second elongated body surrounding said elongate body, and axially aligned therewith for axial adjustment with respect thereto, said frictional engagement device extending from a free end of said second elongated body.

19. The apparatus of claim 16 wherein said manipulation includes selective radial collapse of said frictional engagement device.

20. The apparatus of claim 19 wherein said means for manipulating said frictional engagement device in furtherance of secure capture of the magnetic coupler within said frictional engagement device comprises a second elongate body surrounding said elongate body, and axially aligned therewith for axial adjustment with respect thereto, said frictional engagement device extending from said free end of said elongate body, and thereby being radially collapsible within said second elongate body upon select adjustment of said second elongate body.

21. The apparatus of claim 14 further comprising a second elongate body, said second elongated body surrounding said elongate body, and axially aligned therewith for axial adjustment with respect thereto.

22. The apparatus of claim 21 wherein said means for mechanically retaining the initially attracted and aligned magnetic coupler is a strap, said strap joining said magnetic coupling to a distal portion of said second elongate body such that upon axial translation of said second elongate body, a closure is formed about said magnetic coupling and the attracted magnetic coupler.

23. In a method of conducting minimally invasive medical procedures on a mammalian body, the steps comprising:
   a. providing a medical device equipped with a magnetic coupler;
   b. deploying said medical device within the mammalian body;
   c. providing an advanceable retrieval tool comprising an elongate member equipped with a magnetic coupling at one end thereof, and a frictional engagement device extending from said end of said elongate member, said magnetic coupling being substantially housed therein;
   d. advancing said advanceable retrieval tool toward said medical device such that said magnetic coupler is drawn into said frictional engagement device toward said magnetic coupling so as to mate with said magnetic coupling, said magnetic coupler being trapped within said frictional engagement device so as to be retrieved by said advanceable retrieval tool.

24. The method of claim 23 wherein said magnetic coupler is non-rigidly connected to said medical device.

25. The method of claim 24 wherein a tether joins said magnetic coupler to said medical device.

26. The method of claim 25 wherein further retrieval security is provided via rotation of said tool so as to cause said tether to pull said magnetic coupler into said frictional engagement device.

27. The method of claim 23 comprising the further step of auditory monitoring to detect the mating of said magnetic coupler with said magnetic coupling.

* * * * *